(12) United States Patent
Lee et al.

(10) Patent No.: US 9,964,479 B2
(45) Date of Patent: May 8, 2018

(54) APPARATUS AND METHOD FOR MEASURING SURFACE TENSION

(75) Inventors: Junghoon Lee, Seoul (KR); Yongjoo Kwon, Seoul (KR); Seungyul Choi, Seoul (KR)

(73) Assignee: SEOUL NATIONAL UNIVERSITY R&D FOUNDATION, Seoul (KR)

(*) Notice: Subject to any disclaimer, the term of this patent is extended or adjusted under 35 U.S.C. 154(b) by 900 days.

(21) Appl. No.: 14/367,321

(22) PCT Filed: Dec. 31, 2011

(86) PCT No.: PCT/KR2011/010412
§ 371 (c)(1),
(2), (4) Date: Jun. 20, 2014

(87) PCT Pub. No.: WO2013/100244
PCT Pub. Date: Jul. 4, 2013

(65) Prior Publication Data
US 2015/0233810 A1    Aug. 20, 2015

(30) Foreign Application Priority Data

Dec. 31, 2011 (KR) .................. 10-2011-0147980

(51) Int. Cl.
*G01N 13/02* (2006.01)
*G01N 27/22* (2006.01)

(52) U.S. Cl.
CPC ............ *G01N 13/02* (2013.01); *G01N 27/22* (2013.01); *G01N 2013/0208* (2013.01); *G01N 2013/0241* (2013.01); *G01N 2013/0283* (2013.01)

(58) Field of Classification Search
CPC .......... G01N 13/02; G01N 2013/0208; G01N 2013/0241; G01N 2013/0283
See application file for complete search history.

(56) References Cited

U.S. PATENT DOCUMENTS 5,542,289 A * 8/1996 Hool ................... G01N 13/02
324/691

FOREIGN PATENT DOCUMENTS

JP          2010-078603       4/2010
KR     10-2007-0035727       4/2007
WO       WO 2008-110560       9/2008

OTHER PUBLICATIONS

International Search Report dated Nov. 28, 2012 for PCT/KR2011/010412.
Yongjoo Kwon, Seungyul Choi, and Junghoon Lee, Nov. 2011 "Electrical measurement of Contact angle and Surface tension," Journal of Mechanical Science and Technology, Fall Conference, pp. 1855-1859.

* cited by examiner

*Primary Examiner* — Paul West

(57) ABSTRACT

The present invention relates to an apparatus and method for measuring surface tension. More particularly, the present invention relates an apparatus and method for measuring surface tension through an electrical scheme which is simpler and has improved accuracy compared to a conventional optical scheme.

2 Claims, 3 Drawing Sheets

Fig. 7
Contact Angle & Surface Tension
(Liquid 2: Bromododecane + Chloronaphtalene (1:1), Solid: Parylene)
| Liquid1<br>Tween(wt% in water) | ST(L1-L2)<br>- image -<br>(mN/m) | ST(L1-L2)<br>- diff -<br>(mN/m) | Remarks |
|---|---|---|---|
| 0.0001 | | 19.4 | Calculation range:<br>8~10 volt |
| 0.001 | 14.69 | 14.9 | 7~10 volt |
| 0.01 | | 5.19 | 6~9 volt |
| 0.1 | | 4.14 | 5~8 volt |
| 0.25 | 4.50 | 3.5 | 3~7 volt |
Fig. 8
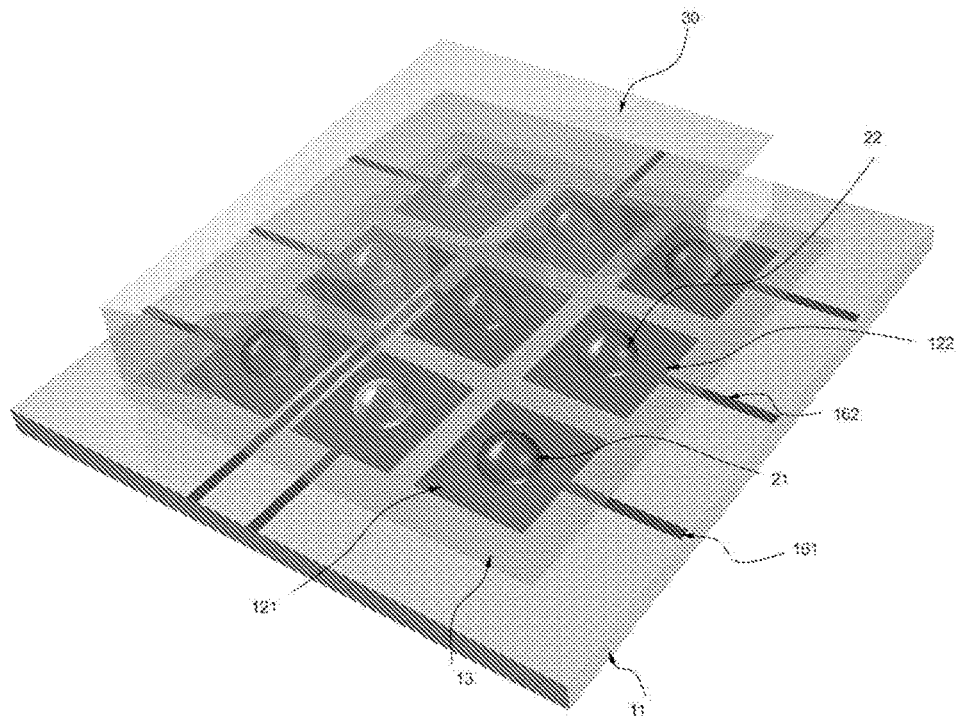
Fig. 9
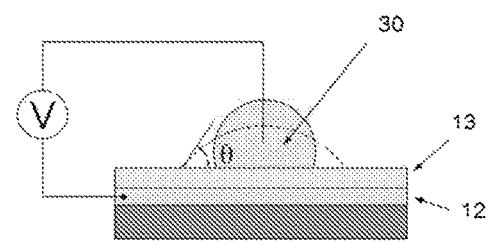

APPARATUS AND METHOD FOR MEASURING SURFACE TENSION

This application claims the priority of Korean Patent Application No. 10-2011-0147980, filed on Dec. 31, 2011 in the KIPO (Korean Intellectual Property Office), the disclosure of which is incorporated herein entirely by reference. Further, this application is the National Stage application of International Application No. PCT/KR2011/010412, filed Dec. 31, 2011, which designates the United States and was published in Korean. Each of these applications is hereby incorporated by reference in their entirety into the present application.

TECHNICAL FIELD

The present disclosure relates to a device and method for measuring surface tension, and more particularly, to a device and method for measuring surface tension more simply and accurately by using an electrical manner in comparison to an existing surface tension measuring method using an optical manner.

BACKGROUND ART

Surface tension means a pulling force of liquids on a surface and has a feature of minimizing the surface by means of intermolecular forces. Liquid molecules apply force to each other. A single liquid molecule receives forces from surrounding molecules in all direction. However, on a surface, there is no force applied from the above. Therefore, a state on a surface is more unstable in comparison to an intermediate location, and in order to minimize such an unstable state, liquid tends to minimize the surface which is in an unstable state.

Such instability may be reduced by applying a force to another particle on the surface. In other words, a balance of intermolecular attractions of a liquid is broken, molecules near the liquid surface have greater potential energy in comparison to molecules inside the liquid, and for this reason, the liquid has energy proportional to the entire surface energy, thereby creating surface tension. Therefore, the surface tension may also be expressed as an equation in relation to the energy applied to a unit area. Actually, the surface tension is expressed by a tension applied to both sides of a line having a unit length. This value is a constant determined according to the kind of liquid but may also vary depending on temperature.

As described above, the surface tension is in form of attractions applied among all molecules located on a surface, and this keeps a balance with a resisting force against compression of the liquid. Therefore, in a physical aspect, the surface tension is applied in a tangential direction of the liquid surface, resultantly forming a curvature of a swelled balloon or bubble.

Generally, the force of surface tension includes a Laplace formula which expresses a pressure jump on a boundary.

If surfaces of two different materials come into contact with each other, a contact angle is formed. At a contact surface with a solid wall, the wetting effect may be expressed using the contact angle. The contact angle represents an angle formed when liquid keeps a thermodynamic equilibrium on a solid surface. At this time, the contact angle varies according to a feature of the fluid or a roughness or shape of the wall.

Such a contact angle is generated by different surface free energy between liquid and solid, between liquid and gas, or between gas and solid. If three different materials come into contact with each other, such a contact angle is generated, and equilibrium is kept at a certain angle by means of each surface free energy. Generally, the contact angle is used as an angle formed by a solid surface and a liquid surface.

However, if fluid moves, such a contact angle changes. This is called a dynamic contact angle. The dynamic contact angle represents an angle formed between solid and fluid surfaces when the fluid flows, and is frequently used when measuring surface tension of a solution. The dynamic contact angle is generally generated by inertia in relation to the movement of fluid.

In order to measure surface tension of a liquid, various studies have been performed.

(1) Capillary rise method. A capillary tube is placed upright in a specimen solution, and a height (h) of the specimen solution rising in the capillary tube is measured. Here, surface tension=rhρg/2, where r represents a diameter of the capillary tube, ρ represents a density of the specimen solution, and g represents an acceleration of gravity.

(2) Stalagmometric method. A stalagmometer (a circular tube having a flat section) is used to quietly drop a specimen solution. Assuming that a single drop has a mass of m, a force of pulling downwards a dropping liquid is mg, and a force of lifting a dropping liquid upwards is 2πγ×(surface tension). γ represents an outer radius of the tube, and the surface tension is calculated by measuring m.

(3) Pendent drop method. A small pellet of platinum is suspended horizontally and brought into contact with a specimen solution, and then when pulling the small pellet of platinum, a force f required for detaching the pellet of a radius γ from a liquid is a double of 2πγ. Surface tension is calculated from f by using a torsion balance. A surface tension measurer of Du Nouy uses this method and is available in the market. In this method, surface tension of a small amount of specimen solution may be measured in a relatively rapid and accurate way.

(4) Stalagmometric comparison method. A stalagmometer is used to drop a certain amount of specimen solution, and the dropped amount (n2) is checked. The same volume of standard solution is dropped using the same stalagmometer, and its dropped amount (n1) is calculated. Assuming that the density of the specimen solution is d2 and the density of the standard solution is d1, surface tension of the specimen solution=surface tension of the standard solution×(n1/n2)×(d2/d1).

FIG. 1 is a representative diagram showing a method for measuring a magnitude of surface tension by using an existing optical method.

The surface tension may be measured according to Equations 1 and 2 below. Here, Ci represents a curvature of a medium i.

$$\rho g \Delta h = \gamma (C_1 - C_2) \quad \text{(Equation 1)}$$

$$\gamma = \frac{\rho g \Delta h}{(C_1 - C_2)} \quad \text{(Equation 2)}$$

When measuring surface tension in this way, an optical method is mostly used, which however has complicated measurement and analysis processes and causes an error.

In the present disclosure, a new method for measuring surface tension is proposed using an electro-wetting property. Electro-wetting means a phenomenon in which when a voltage is applied between a conductive fluid and a bottom electrode as shown in FIG. 9, wettability to the bottom surface of the conductive fluid changes and the conductive fluid spreads on the bottom surface.

DISCLOSURE OF THE INVENTION

Technical Problem

The present disclosure is directed to providing a device and method for measuring surface tension more simply and accurately by using an electrical manner in comparison to an existing surface tension measuring method.

Technical Solution

To solve the above object, the present disclosure provides the following solutions.

In an aspect of the present disclosure, there is provided a device for measuring surface tension, which measures a magnitude of surface tension between a conductive fluid 30 and a nonconductive fluid 20 by using an electric characteristic, the device including: a substrate 11; an electrode 12 formed on the substrate 11; a dielectric layer 13 formed at an upper side of the electrode 12; a container 14 containing the conductive fluid 30 to cover the electrode 12; and a voltage applying unit 40 for applying a voltage between the electrode 12 and the conductive fluid 30, wherein the nonconductive fluid 20 is provided in the container 14 to be located on the electrode 12 inside the conductive fluid 30 so that the dielectric layer 13 is interposed between the nonconductive fluid 20 and the electrode 12, and wherein capacitance according to a geometric shape of the nonconductive fluid 20 is measured to measure a contact angle and surface tension.

In another aspect of the present disclosure, there is provided a device for measuring surface tension, which measures a magnitude of surface tension between a conductive fluid 30 and a nonconductive fluid 20 by using an electric characteristic, the device including: a substrate 11; an electrode 12 formed on the substrate 11; a dielectric layer 13 formed at an upper side of the electrode 12; a container 14 containing the nonconductive fluid 20 to cover the electrode 12, the conductive fluid 30 being provided in the container 14 to be located on the electrode 12 inside the nonconductive fluid 20 so that the dielectric layer 13 is interposed between the conductive fluid 30 and the electrode 12; and a voltage applying unit 40 for applying a voltage between the electrode 12 and the conductive fluid 30, wherein capacitance according to a geometric shape of the conductive fluid 30 is measured to measure a contact angle and surface tension.

In another aspect of the present disclosure, there is provided a device for measuring surface tension, which simultaneously measures surface tension of a plurality of nonconductive fluids 20 by using an electric characteristic, the device including: a substrate 11; a plurality of electrodes spaced apart from each other on the substrate 11; a dielectric layer 13 formed at an upper side of the electrodes; a container containing a conductive fluid 30 to cover the electrodes; and a voltage applying unit for applying a voltage between the electrodes and the conductive fluid 30, wherein the nonconductive fluid is provided in the container to be located on the electrodes inside the conductive fluid 30 so that the dielectric layer 13 is interposed between the nonconductive fluid and the electrodes 12, and wherein capacitance according to a geometric shape of the nonconductive fluid is measured to measure a contact angle and surface tension.

In this case, the device for measuring surface tension may further include a current measuring unit for measuring a current flowing between the electrode 12 and a fluid in the container 14; and a calculating unit for calculating a contact angle and a magnitude of surface tension by using the voltage applied by the voltage applying unit 40 and the current measured by the current measuring unit, wherein the calculating unit may measure capacitance by using Equation 1 and measure a contact angle from the capacitance by using Equation 2:

$$Z = \frac{V}{I} = \frac{V/\varphi_v}{I/\varphi_i} = R_w - j\frac{1}{\omega C_d} = Z/\varphi \qquad \text{Equation 1}$$

$$\varphi = \varphi_v - \varphi_i = \tan^{-1}\frac{-1}{\omega R_{w_1} C_d}$$

where Z represents impedance, R represents resistance of the fluid, C represents capacitance, ω represents frequency of power, and φ represents a phase angle, $$R = \frac{3V^{1/3}}{\pi(2+\cos\theta)(1\ \cos\theta\ )^2} \qquad \text{Equation 2}$$

$$A = \pi R^2 \sin^2\theta$$

$$C = \frac{\varepsilon A}{d}$$

where V represents a volume of the nonconductive fluid, A represents an area of a surface of the nonconductive fluid which is in contact with the dielectric layer, ∈ represents a dielectric constant, d represents a thickness of the dielectric layer, and R and θ are shape values depicted in FIG. 3.

In addition, the calculating unit may calculate a magnitude of surface tension by using any one of Equations 3 to 5:

$$\gamma = \frac{\varepsilon}{d\frac{\partial \cos\theta}{\partial V}} \cdot V \qquad \text{Equation 3}$$

$$\gamma = \frac{\varepsilon}{d\frac{\partial^2 \cos\theta}{\partial V^2}} \qquad \text{Equation 4}$$

$$\gamma = \frac{\epsilon(V_1^2 - V_2^2)}{2d(\cos\theta_1 - \cos\theta_2)} \qquad \text{Equation 5}$$

where θ1 represents a contact angle when a voltage V1 is applied, and θ2 represents a contact angle when a voltage V2 is applied.

In particular, a coating layer 15 made of hydrophobic material may be further formed on the dielectric layer 13.

In another aspect of the present disclosure, there is provided a method for measuring surface tension, which includes: locating a nonconductive fluid 20 in a conductive fluid 30 to form a contact angle with respect to an electrode 12; applying a voltage to the electrode 12 and the conductive fluid 30, and measuring a current flowing between the electrode 12 and the conductive fluid 30 while changing the applied voltage; calculating capacitance according to the contact angle of the nonconductive fluid 20 by using Equation 1; measuring a contact angle θ by using Equation 2; and measuring a magnitude γ of surface tension by using any one of Equations 3 to 5.

In another aspect of the present disclosure, there is provided a method for measuring surface tension, which includes: locating a conductive fluid 30 in a nonconductive fluid 20 to form a contact angle with respect to an electrode 12; applying a voltage to the electrode 12 and the conductive fluid 30, and measuring a current flowing between the electrode 12 and the conductive fluid 30 while changing the applied voltage; calculating capacitance according to the contact angle of the conductive fluid 30 by using Equation 1; measuring a contact angle θ by using Equation 2; and measuring a magnitude γ of surface tension by using any one of Equations 3 to 5.

Advantageous Effects

The present disclosure gives an effect of measuring surface tension more simply and accurately by using an electrical manner in comparison to an existing surface tension measuring method.

BRIEF DESCRIPTION OF THE DRAWINGS

FIG. 7 is a diagram for illustrating an effect of the device for measuring surface tension according to the present disclosure.

FIG. 8 is a diagram showing an embodiment of the device for measuring surface tension according to the present disclosure.

FIG. 9 is a diagram showing another embodiment of the device for measuring surface tension according to the present disclosure.

MODE FOR CARRYING OUT THE INVENTION

Hereinafter, the present disclosure will be described in detail with reference to accompanying drawings.

For better understanding of the present disclosure, any features of the present disclosure already known in the art will not be described in detail here. The following embodiments are just for better understanding of the present disclosure and not intended to limit the scope of the present disclosure. Therefore, any equivalents having the same function as the present disclosure will also fall within the scope of the present disclosure.

In the following explanation, the same reference sign indicates the same component, and details of well-known features and techniques may be omitted.

Figure 1:
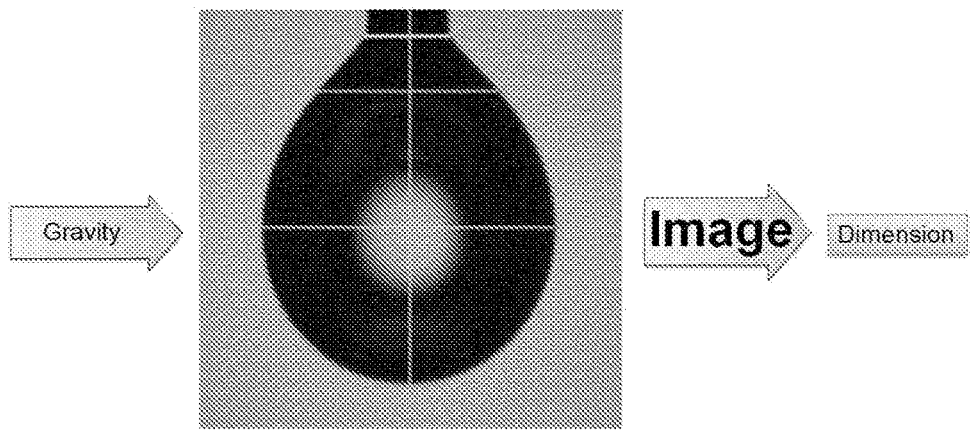
FIG. 1 is a diagram showing an existing method for measuring surface tension.
Figure 2:
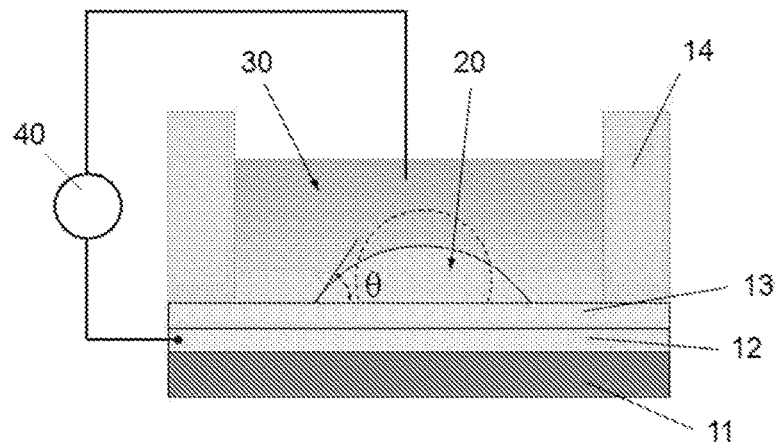
FIG. 2 is a diagram showing a device for measuring surface tension according to the present disclosure.

FIG. 2 is a diagram showing a device for measuring surface tension according to the present disclosure.

According to an embodiment of the present disclosure, a device for measuring surface tension (hereinafter, also referred to as a "surface tension measuring device") measures a magnitude of surface tension between a conductive fluid 30 and a nonconductive fluid 20 by using an electric characteristic.

Even though it is described in the following embodiment that the nonconductive fluid 20 is included in the conductive fluid 30 in a drop form, but the same principle may also be applied even though the nonconductive fluid 20 is included in a drop form in the conductive fluid 30 on the contrary.

According to the present disclosure, the surface tension measuring device includes a substrate 11, an electrode 12 formed on the substrate 11, a dielectric layer 13 formed at an upper side of the electrode 12, a container 14 containing the conductive fluid 30 to cover the electrode 12, and a voltage applying unit 40 for applying a voltage between the electrode 12 and the conductive fluid 30.

Even though the electrode is depicted as a flat electrode, the present disclosure is not limited thereto, and various kinds of electrodes having a V shape, a cylindrical shape, a rectangular well shape or the like may also be used.

However, a dielectric layer may be removed so that the electrode 12 is directly exposed to the container.

The nonconductive fluid 20 is provided in the container 14 to be located on the electrode 12 inside the conductive fluid 30 so that the dielectric layer 13 is interposed between the nonconductive fluid 20 and the electrode 12.

Capacitance according to a geometric shape of the nonconductive fluid 20 is measured to measure a contact angle and surface tension.

The nonconductive fluid 20 is provided to be entirely included in the conductive fluid 30, and there is a pressure difference in a medium between the nonconductive fluid 20 and the conductive fluid 30 due to different surface energies. In this case, the pressure difference forms a curvature to keep a balance on the surface, and the nonconductive fluid 20 has a partial spherical shape as shown in FIG. 2.

In the present disclosure, when the nonconductive fluid 20 forms a contact angle in the conductive fluid 30 and has a partial spherical shape, impedance including capacitance according to the shape is obtained, and a contact angle is calculated therefrom. Generally, in the case of FIG. 2, Equation 3 below is established.

$$\cos\theta = \cos\theta_Y + \frac{\varepsilon}{2\gamma d}V^2 \qquad \text{Equation 3}$$

where θ represents a contact angle changed by electrowetting when a voltage is applied to a fluid, θY represents a contact angle in an equilibrium state, $\in$ represents a dielectric constant, γ represents surface tension, V represents an applied voltage, and d represents a thickness of dielectric material.

This will be described in more detail below.

Figure 3:
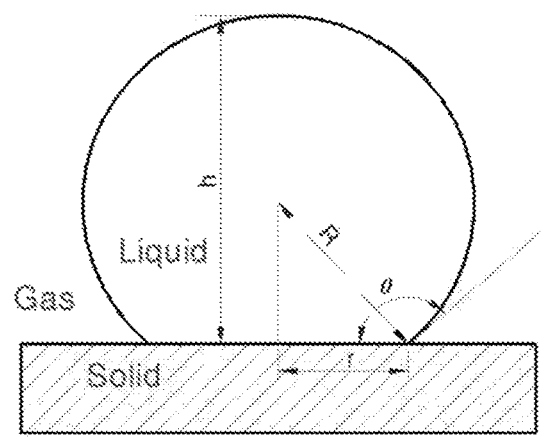
FIG. 3 is a diagram for illustrating the principle of applying the device for measuring surface tension according to the present disclosure.

FIG. 3 shows a figure of the nonconductive fluid 20 which forms a partial spherical shape. Even though FIG. 3 shows a general 3-phase relation, the same concept may also be applied when a liquid is applied to the nonconductive fluid 20, a gas is applied to the conductive fluid 30, and a solid is applied to the dielectric layer or the electrode.

A radius R of the entire sphere changes according to the contact angle of the nonconductive fluid 20, and accordingly an area of a circular shape contacting the dielectric layer also changes. At this time, a radius of the circle of the contact surface is defined as r.

In this case, Equation 4 below is established from the geometrical shape information. In addition, capacitance according to the contact surface of the nonconductive fluid 20 also establishes Equation 4 below. Here, V represents a volume of the nonconductive fluid, A represents an area of a surface of the nonconductive fluid which is in contact with the dielectric layer, c represents a dielectric constant, d represents a thickness of the dielectric layer, and R and θ are shape values depicted in FIG. 3.

$$R = \frac{3V^{1/3}}{\pi(2+\cos\theta)(1-\cos\theta)^2} \quad \text{Equation 4}$$

$$A = \pi R^2 \sin^2\theta$$

$$C = \frac{\varepsilon A}{d}$$

If Equation 4 is arranged, the contact value may also be expressed as a function of capacitance like Equation 5 below.

$$\theta = f(\text{Cap.}) \quad \text{Equation 5}$$

Figure 4:
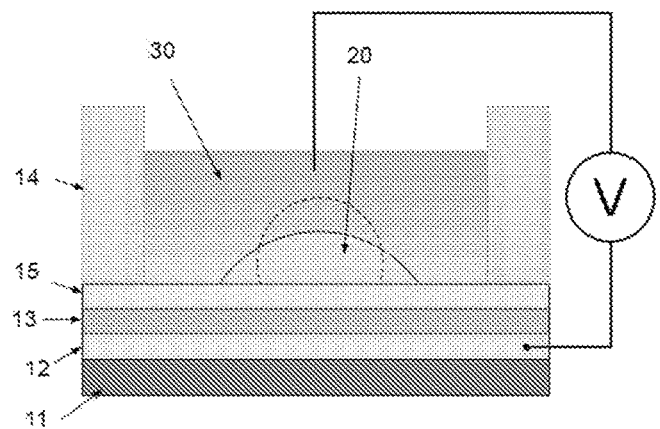
FIG. 4 is a diagram showing a device for measuring surface tension according to the present disclosure.
Figure 5:
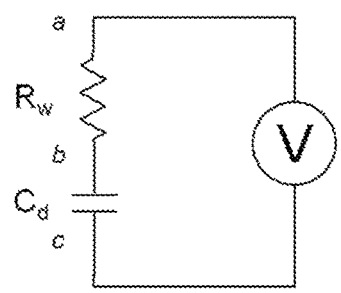
FIG. 5 is a diagram for illustrating the principle of applying the device for measuring surface tension according to the present disclosure.

In the measuring device of FIG. 2 or 4, if a voltage is applied to the electrode 12 and the fluid, the device may be simplified into a circuit of FIG. 5. Rw represents resistance by the fluid, and Cd represents capacitance by the dielectric material.

In this case, the surface tension measuring device may further include a current measuring unit for measuring a current flowing between the electrode 12 and the fluid in the container 14, and a calculating unit for calculating a contact angle and a magnitude of surface tension by using the voltage applied by the voltage applying unit 40 and the current measured by the current measuring unit.

At this time, the calculating unit measures capacitance by using Equation 6 below with the applied voltage and the measured current as input values. Here, Z represents impedance, V represents a voltage, I represents a current, R represents resistance of the fluid, C represents capacitance, ω represents frequency of power, and φ represents a phase angle.

As obvious from the following equation, the voltage and current used in the present disclosure should be AC voltage and current having a magnitude and phase.

$$Z = \frac{V}{I} = \frac{V/\varphi_v}{I/\varphi_i} = R_w - j\frac{1}{\omega C_d} = Z/\varphi \quad \text{Equation 6}$$

$$\varphi = \varphi_v - \varphi_i = \tan^{-1}\frac{-1}{\omega R_w C_d}$$

By obtaining the capacitance through Equation 6, a contact angle may be obtained if the capacitance is applied to Equation 4 above.

After obtaining the contact angle, the contact angle may be applied to Equation 3 to obtain surface tension. However, an equilibrium contact angle is just a constant and may be treated as an unnecessary value in calculation, and thus Equation 3 may be primarily differentiated to induce Equation 7 below. Here, V represents an applied voltage, and θ represents a contact angle at this time.

$$\gamma = \frac{\varepsilon}{d\frac{\partial \cos\theta}{\partial V}} \cdot V \quad \text{Equation 7}$$

The calculating unit includes an algorithm of Equation 7, and performs the above calculation by using the obtained contact angle as an input value. The surface tension obtained through this calculation advantageously has less noise.

In addition, Equation 3 may be secondarily differentiated to induce Equation 8 below. Here, V represents an applied voltage, and θ represents a contact angle at this time.

$$\gamma = \frac{\varepsilon}{d\frac{\partial^2 \cos\theta}{\partial V^2}} \quad \text{Equation 8}$$

Also, the calculating unit includes an algorithm of Equation 8, and performs the above calculation by using the obtained contact angle as an input value. The surface tension obtained through this calculation has noise more or less, but there is substantially no surface charging effect, advantageously.

In addition, the surface tension may also be obtained using Equation 9 below. At this time, after different voltages are applied, contact angles for the voltages are compared to obtain more accurate surface tension. Here, θ1 represents a contact angle when a voltage V1 is applied, and θ2 represents a contact angle when a voltage V2 is applied.

$$\gamma = \frac{\epsilon(V_1^2 - V_2^2)}{2d(\cos\theta_1 - \cos\theta_2)} \quad \text{Equation 9}$$

The calculating unit may selectively use any one of Equations 7 to 9. Though not depicted in the figures, in the calculating unit, the algorithm described above is generally previously set as a combination of a CPU and a memory, and the calculating unit receives an input value and mechanically performs a calculation by using the preset algorithm. This is obvious to those skilled in the art and will not be described in detail here.

The current measuring unit is also not depicted in the figures but obvious to those skilled in the art.

Figure 6:
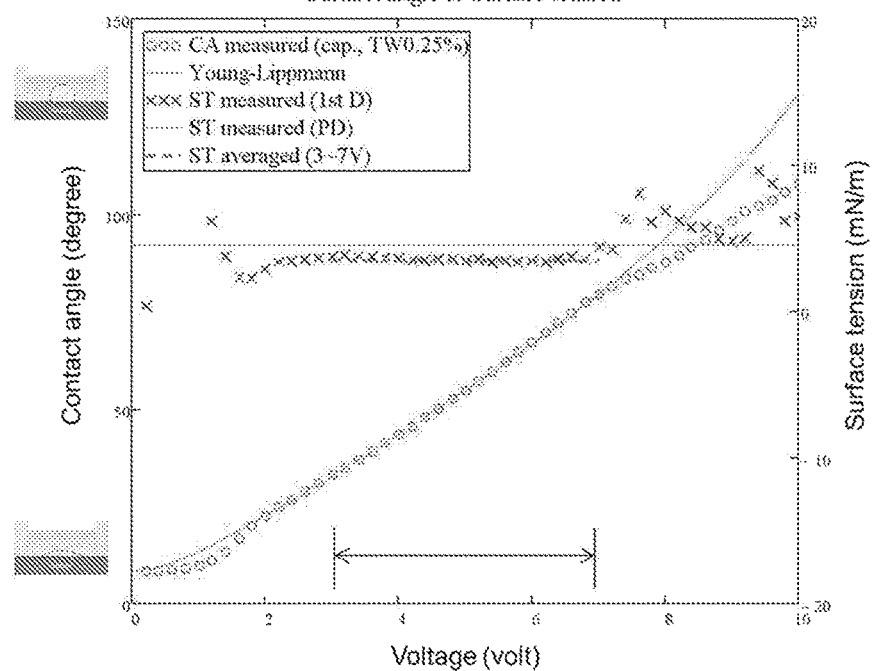
FIG. 6 is a diagram for illustrating an effect of the device for measuring surface tension according to the present disclosure.

FIGS. 6 and 7 show measurement results of the measuring device of the present disclosure, from which it may be found that the measuring device of the present disclosure ensures good accuracy.

In the present disclosure, particularly, a coating layer 15 made of hydrophobic material is further formed on the dielectric layer 13. The coating layer 15 allows the nonconductive fluid 20 present inside the conductive fluid 30 to be located at an upper side of the coating layer 15. By doing so, the fluid subject to measurement is automatically positioned.

FIG. 8 shows another embodiment of the present disclosure. This embodiment is directed to a surface tension measuring device for measuring surface tension of a plurality of nonconductive fluids 20 simultaneously by using an electric characteristic. The surface tension measuring device includes a substrate 11, a plurality of flat electrodes 121, 122 spaced apart from each other on the substrate 11, a dielectric layer 13 formed at an upper side of the electrode 12, a container containing the conductive fluid 30 to cover the electrode 12, and a voltage applying unit 40 for applying a voltage between the electrode 12 and the conductive fluid 30, wherein the nonconductive fluid is provided in the container 14 to be located on the electrode inside the conductive fluid 30 so that the dielectric layer 13 is interposed between the nonconductive fluid 20 and the electrode 12, and wherein capacitance according to a geometric shape of the nonconductive fluid is measured to measure a contact angle and surface tension.

The principle of this embodiment is identical to the former embodiment, but the plurality of electrodes are provided to be electrically separated from each other. The electrodes are individually connected to electrode lines 161, 162 for applying voltages, respectively.

FIG. 9 shows another application of the present disclosure. The surface tension measuring device of this embodiment measures surface tension of the conductive fluid 30. Here, the conductive fluid 30 is located on the electrode 12 in a drop form, and a voltage is directly applied to the conductive fluid 30 so that capacitance varying depending on an area of a contact surface according to the contact angle of the conductive fluid 30 is measured to obtain surface tension. This embodiment is different from the former embodiment in the point that only a single conductive fluid exposed to a gas state is used instead of two kinds of conductive and nonconductive fluids. Its principle is substantially identical to the former embodiment and thus not described in detail here.

A method for measuring surface tension according to the present disclosure includes a first step of locating a nonconductive fluid 20 in a conductive fluid 30 to form a contact angle with respect to an electrode 12, a second step of applying a voltage to the electrode 12 and the conductive fluid 30 and measuring a current flowing between the electrode 12 and the conductive fluid 30 while changing the applied voltage, a third step of calculating capacitance according to the contact angle of the nonconductive fluid 20 by using Equation 6, a fourth step of measuring a contact angle θ by using Equation 4, and a fifth step of measuring a magnitude γ of surface tension by using Equation 7 or 8.

In this specification, the expression "forming a contact angle with respect to an electrode" has a meaning including not only a direct contact onto the electrode but also a contact to a dielectric layer (or, an insulating layer) if the dielectric layer is formed on the upper surface of the electrode. In other words, the same structure as described above may be applied hereto.

In addition, a method for measuring surface tension according to the present disclosure may include a first step of locating a conductive fluid 30 in a nonconductive fluid 20 to form a contact angle with respect to an electrode 12, a second step of applying a voltage to the electrode 12 and the conductive fluid 30 and measuring a current flowing between the electrode 12 and the conductive fluid 30 while changing the applied voltage, a third step of calculating capacitance according to the contact angle of the conductive fluid 30 by using Equation 6, a fourth step of measuring a contact angle θ by using Equation 4, and a fifth step of measuring a magnitude γ of surface tension by using Equation 7 or 8.

Details of this embodiment are substantially identical to the former embodiment and thus not described in detail here.

The term "comprise", "include" or "have" used herein means that any component can be provided therein, unless otherwise stated, and thus should be interpreted as being capable of further including other components, instead of excluding other components. All terms including technical terms or scientific terms have the same meanings as being generally understood by those skilled in the art of the present disclosure, unless otherwise defined. Terms generally used as defined in dictionaries should be interpreted as being in agreement with the context of relevant descriptions, and should not be interpreted too ideally or excessively formally, unless otherwise defined in the present disclosure.

The invention claimed is:

1. A device for measuring surface tension, which measures a magnitude of surface tension between a conductive fluid and a nonconductive fluid by using an electric characteristic, the device comprising:
    a substrate;
    an electrode formed on the substrate;
    a dielectric layer formed at an upper side of the electrode;
    a container containing the conductive fluid to cover the electrode; and
    a voltage applying unit for applying a voltage between the electrode and the conductive fluid,
    wherein the nonconductive fluid is provided in the container to be located on the electrode inside the conductive fluid so that the dielectric layer is interposed between the nonconductive fluid and the electrode, and
    wherein capacitance according to a geometric shape of the nonconductive fluid is measured to measure a contact angle and surface tension.

2. A device for measuring surface tension, which measures a magnitude of surface tension between a conductive fluid and a nonconductive fluid by using an electric characteristic, the device comprising:
    a substrate;
    an electrode formed on the substrate;
    a dielectric layer formed at an upper side of the electrode;
    a container containing the nonconductive fluid to cover the electrode, the conductive fluid being provided in the container to be located on the electrode inside the nonconductive fluid so that the dielectric layer is interposed between the conductive fluid and the electrode; and
    a voltage applying unit for applying a voltage between the electrode and the conductive fluid,
    wherein capacitance according to a geometric shape of the conductive fluid is measured to measure a contact angle and surface tension.

* * * * *